US00PP11158P

United States Patent [19]

Walden

[11] Patent Number: Plant 11,158

[45] Date of Patent: Dec. 21, 1999

[54] FLORIBUNDA ROSE PLANT NAMED 'JACMERED'

[75] Inventor: John K. Walden, Somis, Calif.

[73] Assignee: Bear Creek Gardens, Inc., Medford, Oreg.

[21] Appl. No.: 08/998,862

[22] Filed: Dec. 29, 1997

[51] Int. Cl.[6] ..... A01H 5/00

[52] U.S. Cl. ..... Plt./151

[58] Field of Search ..... Plt./150, 151, 129, Plt./122, 141

*Primary Examiner*—Howard J. Locker

*Attorney, Agent, or Firm*—Klarquist Sparkman Campbell Leigh & Whinston, LLP

[57] ABSTRACT

Floribunda rose plant having blooms of a stable, bright red color, singly and in clusters; dark green, semi-glossy foliage; resistant to powdery mildew; and vigorous growth.

1 Drawing Sheet

The present invention relates to a new and distinct variety of rose plant of the floribunda rose class which was originated by me by crossing two unnamed seedlings.

The primary objective of this breeding was to produce a new floribunda rose variety adapted to be grown in pots and having the bright red color, bud form and upright spreading habit of the unnamed female parent combined with the dark green, glossy foliage and clustering of buds and blooms of both the male and female parents, and the petal substance of the male parent. The objective was substantially achieved, along with other desirable improvements, as evidenced by the following unique combination of characteristics that are outstanding in the new variety and that distinguish it from its parents, as well as from all other varieties of which I am aware:

1. Two to two and one-half inch, bright red flowers with very good petal substance;
2. Dark green, semi-glossy foliage;
3. Upright spreading habit; and
4. Clusters of buds in groups of three or more.

Asexual reproduction of this new variety by cutting propagation, as performed at Wasco and Somis, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—Unnamed seedling.

*Pollen parent.*—Unnamed seedling.

Classification:

*Botanical.*—Rosa hybrida.

*Commercial.*—Floribunda rose.

FLOWER

Observations made from specimens grown in a greenhouse environment at Somis, Calif. from April, 1996 to September, 1997.

Blooming habit: Recurrent.

Bud:

*Size.*—Five-eighths inch long when the petals start to unfurl.

*Form.*—The bud form is short, pointed ovoid.

*Color.*—When sepals first divide, bud color is Red-purple Group 60B. When half blown, the upper sides of the petals are Red Group 53A; and the lower sides of the petals are Red-purple Group 63A.

*Sepals.*—Color: Yellow-green group 146B. Surface texture: Smooth with a few very small glandular structures. There are three normally appendaged sepals. There are two unappendaged sepals with hairy edges. The central bud in a cluster often has three foliated and/or bearded sepals and two sepals with hairy edges.

*Receptacle.*—Color: Yellow-green Group 144B. Shape: Funnel. Size: Small (3/16"). Surface: Smooth.

*Peduncle.*—Length: Short (1¾"). Surface: Rough, glandular. Color: Light green with occasional light bronzing. Strength: Stiff, bending, slender.

*Opening.*—Slowly with loose spiral.

Bloom:

*Size.*—Small. Average open size is 2¼ to 2½ inches. Minimum is about 2 inches.

*Borne.*—Singly and several togeher in clusters of three to five flowers.

*Stems.*—Short, about 8–10 inches.

*Form.*—When first open: High centered. Permanence: Outer petal edges curl slightly.

*Petalage.*—Number of petals under normal conditions: 50–60.

*Color.*—The upper sides of the petals are close to Red Group 45A. The reverse sides of the petals are close to Red-purple Group 63A. The base of each petal is Orange-white Group 159D. The major color on the upper sides is close to Red Group 45A.

*Variegations.*—An occasional near-white stripe along mid-vein of the petal.

*Discoloration.*—At the end of the first day: Red Group 46A. At the end of the third day: Red Group 45A with some black tone.

*Fragrance.*—Slight.

Petals:

*Texture.*—Leathery.

*Shape.*—Deltoid.

*Form.*—Moderately quilled.

*Arrangement.*—Slightly quartered to imbricated. Petaloids in the center are few (3 to 7) and small.

*Persistence.*—Drop off cleanly.

*Lastingness.*—On the plant: Long (about 14 days). As a cut flower: Fair (7 to 9 days).

Reproductive parts:

*Anthers.*—Size: Medium. Quantity: Many. Color: Yellow. Arrangement: Regular around styles.

*Filaments.*—Color: Yellow.

*Pollen.*—Color: Lemon yellow.

*Styles.*—Color: Red, Red Group 46A.

*Stigmas.*—Color: White.

Plant:

*Form.*—Bush. Average height is 16 inches, average spread is 14 inches.

*Growth.*—Vigorous; upright; branching.

Foliage: Number of leaflets on normal mid-stem leaves: Five.

*Size.*—Medium (4" long×2½" wide).

*Quantity.*—Normal.

*Color.*—New foliage: Upper and lower surfaces: Red-brown (Greyed-purple Group 183B) over green. Old foliage: Upper surface: Green Group 137A. Lower surface: Yellow-green Group 147B.

*Shape.*—Broadly oval.

*Texture.*—Upper side: Semi-glossy, smooth.

*Edge.*—Serrated.

*Serration.*—Single.

*Petiole rachis.*—Color: Green, with edges of Greyed-Red 179A.

*Petiole underside.*—Smooth, with prickles.

*Stipules.*—Medium, serrated.

*Disease resistance.*—Resistant to mildew under normal growing conditions in the greenhouse at Somis, Calif.

Wood:

*New wood.*—Color: Light green (Yellow-green Group 146C), with reddish tint of Greyed-red Group 181A. Bark: Smooth.

*Old wood.*—Color: Green (Green Group 137B). Bark: Smooth.

Prickles:

*Quantity.*—On main canes from base: Ordinary. On laterals from main canes: Ordinary.

*Form.*—Short (¼"), straight to slightly hooked downward.

*Color when young.*—Reddish (Red Group 46A) at base and near Yellow-Green 154D near tip.

Small prickles:

*Quantity.*—On main stalks: None. On laterals: None.

I claim:

1. A new and distinct variety of rose plant of the floribunda rose class substantially as herein shown and described, characterized particularly as to novelty by blooms of a stable, bright red color, blooming singly and in multiple, small clusters of three to five buds; dark green, semi-glossy foliage; resistance to powdery mildew; and vigorous plant growth.

* * * * *

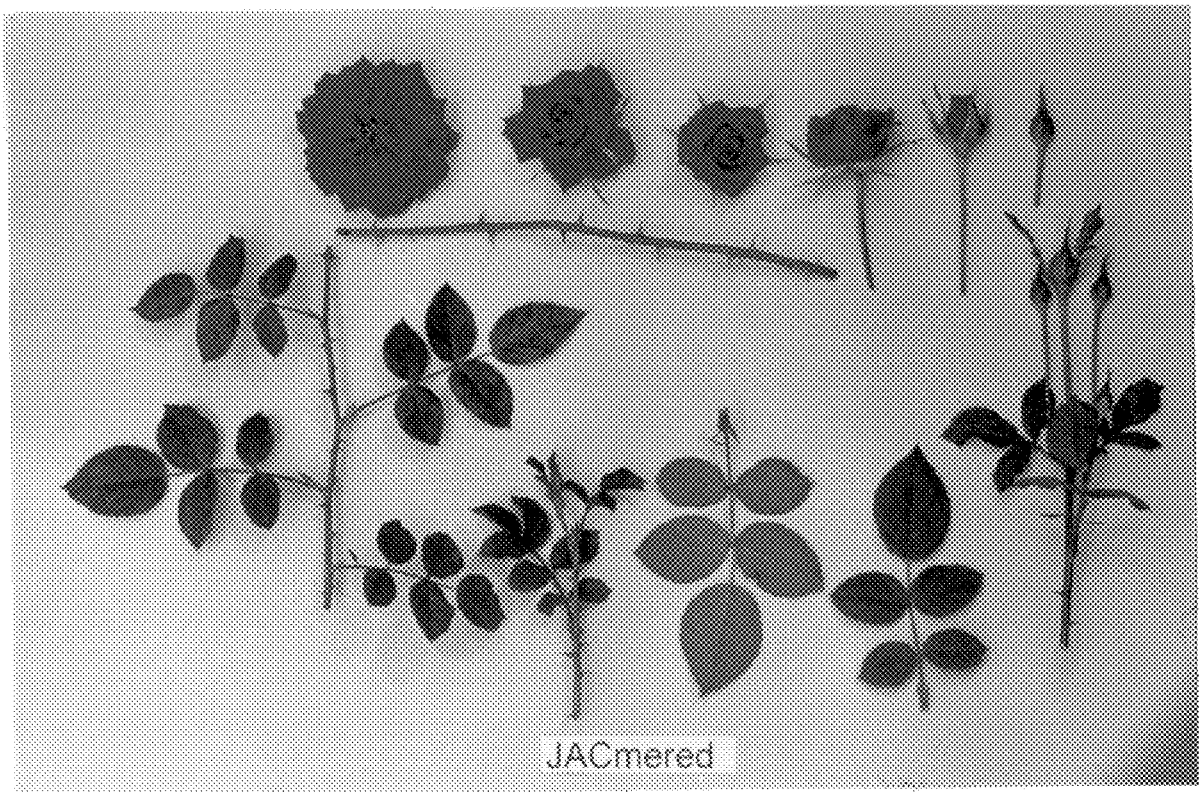
JACmered